US009969725B2

(12) United States Patent
McNevin et al.

(10) Patent No.: US 9,969,725 B2
(45) Date of Patent: May 15, 2018

(54) PHARMACEUTICAL SALTS OF AN OREXIN RECEPTOR ANTAGONIST (71) Applicant: MERCK SHARP & DOHME CORP., Rahway, NJ (US)

(72) Inventors: Michael McNevin, Doylestown, PA (US); Sachin Lohani, Lansdale, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days. days.

(21) Appl. No.: 15/305,246

(22) PCT Filed: Apr. 16, 2015

(86) PCT No.: PCT/US2015/026060
§ 371 (c)(1),
(2) Date: Oct. 19, 2016

(87) PCT Pub. No.: WO2015/164160
PCT Pub. Date: Oct. 29, 2015

(65) Prior Publication Data
US 2017/0044149 A1 Feb. 16, 2017

Related U.S. Application Data (60) Provisional application No. 61/981,889, filed on Apr. 21, 2014.

(51) Int. Cl.
| C07D 249/06 | (2006.01) |
| C07D 413/14 | (2006.01) |
| A61K 31/551 | (2006.01) |
| C07C 305/04 | (2006.01) |
| C07C 309/04 | (2006.01) |
| C07C 309/30 | (2006.01) |
| C07C 305/06 | (2006.01) |
| C07C 309/66 | (2006.01) |

(52) U.S. Cl.
CPC .......... *C07D 413/14* (2013.01); *A61K 31/551* (2013.01); *C07C 305/04* (2013.01); *C07C 305/06* (2013.01); *C07C 309/04* (2013.01); *C07C 309/30* (2013.01); *C07C 309/66* (2013.01); *C07B 2200/13* (2013.01)

(58) Field of Classification Search
CPC .................................................... C07D 249/06
See application file for complete search history.

(56) References Cited

U.S. PATENT DOCUMENTS

| 7,951,797 B2* | 5/2011 | Breslin ................ C07D 401/14 514/218 |
| 9,108,959 B2 | 8/2015 | Baxter et al. |
| 2008/0132490 A1 | 6/2008 | Bergman et al. |
| 2009/0124603 A1 | 5/2009 | Brashear et al. |
| 2013/0331379 A1* | 12/2013 | Baxter ................ C07D 249/06 514/218 |
| 2015/0190402 A1* | 7/2015 | Harmon ............... A61K 31/551 424/78.32 |

FOREIGN PATENT DOCUMENTS

| WO | WO2012148553 | 11/2012 |
| WO | WO2015180060 | 6/2013 |
| WO | WO2013169610 | 11/2013 |
| WO | WO2013181174 | 12/2013 |
| WO | WO2014072961 A3 | 7/2014 |
| WO | WO2016127962 | 8/2016 |

OTHER PUBLICATIONS

Baxter et al., The First Large-Scale synthesis of MK-4305: A Dual Orexin Receptor Antagonist for the Treatment of Sleep Disorder, Organic Process and Research & Development, 2011, 367-375, vol. 15 No. 2.
Carl R. Hopkins, ACS Chemical Neuroscience Molecule Spotlight on Suvorexant, ACS Chem. Neuroscience, 2012, 647-648, 3.
Cox, et al., "Discovery of the Dual Orexin Receptor Antagonist [(7R)-4-(5-Chloro-1,3-benzoxazol-2-yl)-7-methyl-1, 4diazepan . . . ", J. Met Chem, 2010, 5320-5332, vol. 53, No. 14.
I. Mangion et al, Enantioselective Synthesis of a Dual Orexin Receptor Antagonist, Org. Letters, 2012, 3458-3461, 14(13).
Jan K. Mangion, A concise synthesis of a beta-lactarnase Inhibitor, Organic Letters, 2011, 5480-5483, 13(20).
Radi, Suvorexant, Drugs of The Future, 2013, 27-36, 38(1).
Sullivan, Update on Emerging Drugs for Insomia, Expert Opin. Emerging Drugs, 2012, 295-298, 17(3).
Strotman et al., Reaction Development and Mechanistic Study of a Ruthenium Catalyzed Intramolecular Asymmetric Reductive Amination en Route to the Dual Orexin Inhibitor Suvorexant (MK-4305), Am. Chem. Soc., 2011, pp. 8362-8371, vol. 133, No. 21.
"Pharmaceutical Salts", May 1, 1958 (May 1, 1958), pp. 334-335, XP055136472, Retrieved from the Internet: URL://phoenix.tuwien.ac.at/pdf/pharmaceutical_salts/Pharmaceutical_salts.pdf [retrieved on Aug. 26, 2014]*Dodecylsulfuric acid, Hydrochloric acid, Methanesulfonic acid, p-Toluenesulfonic acid*: p. 334.
Kocienski, Synthesis of Suvorexant, Synfacts, 2011, 822, 8.
Kocienski, Synthesis of Suvorexant, Synfacts, 2012, 1049, 8(10).
Lokesh Kumar, An overview of automated systems relevan in pharmaceutical salt screening, Drug Discovery Today, 2007, 1046-1053, 12, No. 23-24.
Saal, C., Pharmaceutical Salts: A summary on doses of salt formers from the Orange Book, European Journal of Pharmaceutical Sciences, 2013, 613-623, 49; No. 4.

(Continued)

*Primary Examiner* — Bruck Kifle
(74) *Attorney, Agent, or Firm* — J. Eric Thies; John C. Todaro (57) ABSTRACT

The invention is directed to pharmaceutically acceptable salts of suvorexant, which is an antagonist of orexin receptors. The pharmaceutically acceptable salts of suvorexant are useful in the treatment or prevention of neurological and psychiatric disorders and diseases in which orexin receptors are involved. The invention is further directed to pharmaceutical compositions comprising pharmaceutically acceptable salts of suvorexant.

17 Claims, 6 Drawing Sheets

(56) References Cited

OTHER PUBLICATIONS

EP Search Report for EP Appln. No. 15782608.2, dated Nov. 30, 2017; 13 pages.
International Search Report and Written Opinion for PCT/US2015/26060 dated Jul. 2, 2015, 10 pages.

* cited by examiner

PHARMACEUTICAL SALTS OF AN OREXIN RECEPTOR ANTAGONIST

CROSS REFERENCE TO RELATED APPLICATIONS

This application is a U.S. National Phase application under 35 U.S.C. § 371 of PCT Application No. PCT/US2015/026060, filed Apr. 16, 2015, which claims priority under 35 U.S.C. § 119(e) from U.S. Ser. No. 61/981,889, filed Apr. 21, 2014.

BACKGROUND OF THE INVENTION

The orexins (hypocretins) comprise two neuropeptides produced in the hypothalamus: the orexin A (OX-A) (a 33 amino acid peptide) and the orexin B (OX-B) (a 28 amino acid peptide) (Sakurai T. et al., Cell, 1998, 92, 573-585). Orexins are found to stimulate food consumption in rats suggesting a physiological role for these peptides as mediators in the central feedback mechanism that regulates feeding behavior (Sakurai T. et al., Cell, 1998, 92, 573-585). Orexins regulate states of sleep and wakefulness opening potentially novel therapeutic approaches for narcoleptic or insomniac patients (Chemelli R. M. et al., Cell, 1999, 98, 437-451). Orexins have also been indicated as playing a role in arousal, reward, learning and memory (Harris, et al., Trends Neurosci., 2006, 29 (10), 571-577). Two orexin receptors have been cloned and characterized in mammals. They belong to the super family of G-protein coupled receptors (Sakurai T. et al., Cell, 1998, 92, 573-585): the orexin-1 receptor (OX or OX1R) is selective for OX-A and the orexin-2 receptor (OX2 or OX2R) is capable to bind OX-A as well as OX-B. The physiological actions in which orexins are presumed to participate are thought to be expressed via one or both of OX 1 receptor and OX 2 receptor as the two subtypes of orexin receptors.

Orexin receptors are found in the mammalian brain and the scientific literature suggests that they may be involved in various pathologies such as depression; anxiety; addictions; obsessive compulsive disorder; affective neurosis; depressive neurosis; anxiety neurosis; dysthymic disorder; behaviour disorder; mood disorder; sexual dysfunction; psychosexual dysfunction; sex disorder; schizophrenia; manic depression; delirium; dementia; severe mental retardation and dyskinesias such as Huntington's disease and Tourette syndrome; eating disorders such as anorexia, bulimia, cachexia, and obesity; addictive feeding behaviors; binge/purge feeding behaviors; cardiovascular diseases; diabetes; appetite/taste disorders; emesis, vomiting, nausea; asthma; cancer; Parkinson's disease; Cushing's syndrome/disease; basophile adenoma; prolactinoma; hyperprolactinemia; hypophysis tumour/adenoma; hypothalamic diseases; inflammatory bowel disease; gastric diskinesia; gastric ulcers; Froehlich's syndrome; adrenohypophysis disease; hypophysis disease; adrenohypophysis hypofunction; adrenohypophysis hyperfunction; hypothalamic hypogonadism; Kallman's syndrome (anosmia, hyposmia); functional or psychogenic amenorrhea; hypopituitarism; hypothalamic hypothyroidism; hypothalamic-adrenal dysfunction; idiopathic hyperprolactinemia; hypothalamic disorders of growth hormone deficiency; idiopathic growth deficiency; dwarfism; gigantism; acromegaly; disturbed biological and circadian rhythms; sleep disturbances associated with diseases such as neurological disorders, neuropathic pain and restless leg syndrome; heart and lung diseases, acute and congestive heart failure; hypotension; hypertension; urinary retention; osteoporosis; angina pectoris; myocardinal infarction; ischemic or haemorrhagic stroke; subarachnoid haemorrhage; ulcers; allergies; benign prostatic hypertrophy; chronic renal failure; renal disease; impaired glucose tolerance; migraine; hyperalgesia; pain; enhanced or exaggerated sensitivity to pain such as hyperalgesia, causalgia, and allodynia; acute pain; burn pain; atypical facial pain; neuropathic pain; back pain; complex regional pain syndrome I and II; arthritic pain; sports injury pain; pain related to infection e.g. HIV, post-chemotherapy pain; post-stroke pain; post-operative pain; neuralgia; emesis, nausea, vomiting; conditions associated with visceral pain such as irritable bowel syndrome, and angina; migraine; urinary bladder incontinence e.g. urge incontinence; tolerance to narcotics or withdrawal from narcotics; sleep disorders; sleep apnea; narcolepsy; insomnia; parasomnia; jet lag syndrome; and neurodegenerative disorders including nosological entities such as disinhibition-dementia-parkinsonism-amyotrophy complex; pallido-ponto-nigral degeneration; epilepsy; seizure disorders and other diseases related to general orexin system dysfunction.

The compound of the formula I:

(also known as "suvorexant") is disclosed as an antagonist of orexin receptors in U.S. Pat. No. 7,951,797, US Patent Application Publication US 2008/0132490, PCT Patent Publication WO 2008/069997, PCT Patent Publication WO 2012/148553, US Patent Application Publication US 2013/0331379, PCT Patent Publication WO 2013/042959, Cox et al., J. Med. Chem. 2010, 53, 5320-5332, Strotman et al., JACS, 2011, 133(21), 8362-8371, Baxter et al., Org. Process Res. & Dev., 2011, 15(2) 367-375. This compound may be named as, e.g., "5-chloro-2-{(5R)-5-methyl-4-[5-methyl-2-(2H-1,2,3-triazol-2-yl)benzoyl]-1,4-diazepan-1-yl}-1,3-benzoxazole," "[(R)-4-(5-chloro-benzooxazol-2-yl)-7-methyl-[1,4]diazepan-1-yl]-(5-methyl-2-[1,2,3]triazol-2-yl-phenyl)-methanone" or "[(7R)-4-(5-chloro-1,3-benzoxazol-2-yl)-7-methyl-1,4-diazepan-1-yl][5-methyl-2-(2H-1,2,3-triazol-2-yl)phenyl]-methanone."

SUMMARY OF THE INVENTION

The invention is directed to pharmaceutically acceptable salts of suvorexant, which is an antagonist of orexin receptors. The pharmaceutically acceptable salts of suvorexant are useful in the treatment or prevention of neurological and psychiatric disorders and diseases in which orexin receptors are involved. The invention is further directed to pharmaceutical compositions comprising pharmaceutically acceptable salts of suvorexant.

DETAILED DESCRIPTION OF THE INVENTION

The invention is directed to pharmaceutically acceptable salts of suvorexant. An embodiment of the invention is directed suvorexant hydrochloride. In an alternate embodiment, the invention is directed to an isolated form of suvorexant hydrochloride. In an alternate embodiment, the invention is directed to a crystalline form of suvorexant hydrochloride. In an alternate embodiment, the invention is directed to an isolated crystalline form of suvorexant hydrochloride.

In an alternate embodiment, the invention is directed to suvorexant hydrochloride isolated in a form which contains at least about 40 wt. % of the crystalline form. In an alternate embodiment, the invention is directed to suvorexant hydrochloride isolated in a form which contains at least about 50 wt. % of the crystalline form. In an alternate embodiment, the invention is directed to suvorexant hydrochloride isolated in a form which contains at least about 60 wt. % of the crystalline form. In an alternate embodiment, the invention is directed to suvorexant hydrochloride isolated in a form which contains at least about 70 wt. % of the crystalline form. In an alternate embodiment, the invention is directed to suvorexant hydrochloride isolated in a form which contains at least about 80 wt. % of the crystalline form. In an alternate embodiment, the invention is directed to suvorexant hydrochloride isolated in a form which contains at least about 90 wt. % of the crystalline form. In an alternate embodiment, the invention is directed to suvorexant hydrochloride isolated in a form which contains at least about 95 wt. % of the crystalline form. In an alternate embodiment, the invention is directed to suvorexant hydrochloride isolated in a form which contains at least about 98 wt. % of the crystalline form. In an alternate embodiment, the invention is directed to suvorexant hydrochloride isolated in a form which contains at least about 99 wt. % of the crystalline form.

In an alternate embodiment, the invention is directed to a pharmaceutical composition that comprises suvorexant hydrochloride. In an alternate embodiment, the invention is directed to a pharmaceutical composition that comprises suvorexant hydrochloride in a form which is at least about 40 wt. % of the crystalline form. In an alternate embodiment, the invention is directed to a pharmaceutical composition that comprises suvorexant hydrochloride in a form which is at least about 50 wt. % of the crystalline form. In an alternate embodiment, the invention is directed to a pharmaceutical composition that comprises suvorexant hydrochloride in a form which is at least about 60 wt. % of the crystalline form. In an alternate embodiment, the invention is directed to a pharmaceutical composition that comprises suvorexant hydrochloride in a form which is at least about 70 wt. % of the crystalline form. In an alternate embodiment, the invention is directed to a pharmaceutical composition that comprises suvorexant hydrochloride in a form which is at least about 80 wt. % of the crystalline form. In an alternate embodiment, the invention is directed to a pharmaceutical composition that comprises suvorexant hydrochloride in a form which is at least about 90 wt. % of the crystalline form. In an alternate embodiment, the invention is directed to a pharmaceutical composition that comprises suvorexant hydrochloride in a form which is at least about 95 wt. % of the crystalline form. In an alternate embodiment, the invention is directed to a pharmaceutical composition that comprises suvorexant hydrochloride in a form which is at least about 98 wt. % of the crystalline form. In an alternate embodiment, the invention is directed to a pharmaceutical composition that comprises suvorexant hydrochloride in a form which is at least about 99 wt. % of the crystalline form.

In an alternate embodiment, the invention is directed to an anhydrous form of suvorexant hydrochloride. In an embodiment, the invention is directed to an anhydrous crystalline form of suvorexant hydrochloride.

In an alternate embodiment, the invention is directed to suvorexant hydrochloride as a solvate. In an alternate embodiment, the invention is directed to suvorexant hydrochloride methanol solvate. In an alternate embodiment, the invention is directed to crystalline suvorexant hydrochloride methanol solvate. In an alternate embodiment, the invention is directed to isolated crystalline suvorexant hydrochloride methanol solvate. In an alternate embodiment, the invention is directed to suvorexant hydrochloride ethanol solvate. In an alternate embodiment, the invention is directed to crystalline suvorexant hydrochloride ethanol solvate. In an alternate embodiment, the invention is directed to isolated crystalline suvorexant hydrochloride ethanol solvate.

An embodiment of the invention is directed suvorexant methanesulfonate. In an alternate embodiment, the invention is directed to an isolated form of suvorexant methanesulfonate. In an alternate embodiment, the invention is directed to a crystalline form of suvorexant methanesulfonate. In an alternate embodiment, the invention is directed to an isolated crystalline form of suvorexant methanesulfonate.

In an alternate embodiment, the invention is directed to suvorexant methanesulfonate isolated in a form which contains at least about 40 wt. % of the crystalline form. In an alternate embodiment, the invention is directed to suvorexant methanesulfonate isolated in a form which contains at least about 50 wt. % of the crystalline form. In an alternate embodiment, the invention is directed to suvorexant methanesulfonate isolated in a form which contains at least about 60 wt. % of the crystalline form. In an alternate embodiment, the invention is directed to suvorexant methanesulfonate isolated in a form which contains at least about 70 wt. % of the crystalline form. In an alternate embodiment, the invention is directed to suvorexant methanesulfonate isolated in a form which contains at least about 80 wt. % of the crystalline form. In an alternate embodiment, the invention is directed to suvorexant methanesulfonate isolated in a form which contains at least about 90 wt. % of the crystalline form. In an alternate embodiment, the invention is directed to suvorexant methanesulfonate isolated in a form which contains at least about 95 wt. % of the crystalline form. In an alternate embodiment, the invention is directed to suvorexant methanesulfonate isolated in a form which contains at least about 98 wt. % of the crystalline form. In an alternate embodiment, the invention is directed to suvorexant methanesulfonate isolated in a form which contains at least about 99 wt. % of the crystalline form.

In an alternate embodiment, the invention is directed to a pharmaceutical composition that comprises suvorexant methanesulfonate. In an alternate embodiment, the invention is directed to a pharmaceutical composition that comprises suvorexant methanesulfonate in a form which is at least about 40 wt. % of the crystalline form. In an alternate embodiment, the invention is directed to a pharmaceutical composition that comprises suvorexant methanesulfonate in a form which is at least about 50 wt. % of the crystalline form. In an alternate embodiment, the invention is directed to a pharmaceutical composition that comprises suvorexant methanesulfonate in a form which is at least about 60 wt. % of the crystalline form. In an alternate embodiment, the invention is directed to a pharmaceutical composition that comprises suvorexant methanesulfonate in a form which is at least about 70 wt. % of the crystalline form. In an alternate embodiment, the invention is directed to a pharmaceutical composition that comprises suvorexant methanesulfonate in a form which is at least about 80 wt. % of the crystalline form. In an alternate embodiment, the invention is directed to a pharmaceutical composition that comprises suvorexant methanesulfonate in a form which is at least about 90 wt. % of the crystalline form. In an alternate embodiment, the invention is directed to a pharmaceutical composition that comprises suvorexant methanesulfonate in a form which is at least about 95 wt. % of the crystalline form. In an alternate embodiment, the invention is directed to a pharmaceutical composition that comprises suvorexant methanesulfonate in a form which is at least about 98 wt. % of the crystalline form. In an alternate embodiment, the invention is directed to a pharmaceutical composition that comprises suvorexant methanesulfonate in a form which is at least about 99 wt. % of the crystalline form.

An embodiment of the invention is directed suvorexant p-toluenesulfonate. In an alternate embodiment, the invention is directed to an isolated form of suvorexant p-toluenesulfonate. In an alternate embodiment, the invention is directed to a crystalline form of suvorexant p-toluenesulfonate. In an alternate embodiment, the invention is directed to an isolated crystalline form of suvorexant p-toluenesulfonate.

In an alternate embodiment, the invention is directed to suvorexant p-toluenesulfonate isolated in a form which contains at least about 40 wt. % of the crystalline form. In an alternate embodiment, the invention is directed to suvorexant p-toluenesulfonate isolated in a form which contains at least about 50 wt. % of the crystalline form. In an alternate embodiment, the invention is directed to suvorexant p-toluenesulfonate isolated in a form which contains at least about 60 wt. % of the crystalline form. In an alternate embodiment, the invention is directed to suvorexant p-toluenesulfonate isolated in a form which contains at least about 70 wt. % of the crystalline form. In an alternate embodiment, the invention is directed to suvorexant p-toluenesulfonate isolated in a form which contains at least about 80 wt. % of the crystalline form. In an alternate embodiment, the invention is directed to suvorexant p-toluenesulfonate isolated in a form which contains at least about 90 wt. % of the crystalline form. In an alternate embodiment, the invention is directed to suvorexant p-toluenesulfonate isolated in a form which contains at least about 95 wt. % of the crystalline form. In an alternate embodiment, the invention is directed to suvorexant p-toluenesulfonate isolated in a form which contains at least about 98 wt. % of the crystalline form. In an alternate embodiment, the invention is directed to suvorexant p-toluenesulfonate isolated in a form which contains at least about 99 wt. % of the crystalline form.

In an alternate embodiment, the invention is directed to a pharmaceutical composition that comprises suvorexant p-toluenesulfonate. In an alternate embodiment, the invention is directed to a pharmaceutical composition that comprises suvorexant p-toluenesulfonate in a form which is at least about 40 wt. % of the crystalline form. In an alternate embodiment, the invention is directed to a pharmaceutical composition that comprises suvorexant p-toluenesulfonate in a form which is at least about 50 wt. % of the crystalline form. In an alternate embodiment, the invention is directed to a pharmaceutical composition that comprises suvorexant p-toluenesulfonate in a form which is at least about 60 wt. % of the crystalline form. In an alternate embodiment, the invention is directed to a pharmaceutical composition that comprises suvorexant p-toluenesulfonate in a form which is at least about 70 wt. % of the crystalline form. In an alternate embodiment, the invention is directed to a pharmaceutical composition that comprises suvorexant p-toluenesulfonate in a form which is at least about 80 wt. % of the crystalline form. In an alternate embodiment, the invention is directed to a pharmaceutical composition that comprises suvorexant p-toluenesulfonate in a form which is at least about 90 wt. % of the crystalline form. In an alternate embodiment, the invention is directed to a pharmaceutical composition that comprises suvorexant p-toluenesulfonate in a form which is at least about 95 wt. % of the crystalline form. In an alternate embodiment, the invention is directed to a pharmaceutical composition that comprises suvorexant p-toluenesulfonate in a form which is at least about 98 wt. % of the crystalline form. In an alternate embodiment, the invention is directed to a pharmaceutical composition that comprises suvorexant p-toluenesulfonate in a form which is at least about 99 wt. % of the crystalline form.

An embodiment of the invention is directed suvorexant dodecyl sulfate. In an alternate embodiment, the invention is directed to an isolated form of suvorexant dodecyl sulfate. In an alternate embodiment, the invention is directed to a crystalline form of suvorexant p-dodecyl sulfate. In an alternate embodiment, the invention is directed to an isolated crystalline form of suvorexant dodecyl sulfate.

In an alternate embodiment, the invention is directed to suvorexant dodecyl sulfate isolated in a form which contains at least about 40 wt. % of the crystalline form. In an alternate embodiment, the invention is directed to suvorexant dodecyl sulfate isolated in a form which contains at least about 50 wt. % of the crystalline form. In an alternate embodiment, the invention is directed to suvorexant dodecyl sulfate isolated in a form which contains at least about 60 wt. % of the crystalline form. In an alternate embodiment, the invention is directed to suvorexant dodecyl sulfate isolated in a form which contains at least about 70 wt. % of the crystalline form. In an alternate embodiment, the invention is directed to suvorexant dodecyl sulfate isolated in a form which contains at least about 80 wt. % of the crystalline form. In an alternate embodiment, the invention is directed to suvorexant dodecyl sulfate isolated in a form which contains at least about 90 wt. % of the crystalline form. In an alternate embodiment, the invention is directed to suvorexant dodecyl sulfate isolated in a form which contains at least about 95 wt. % of the crystalline form. In an alternate embodiment, the invention is directed to suvorexant dodecyl sulfate isolated in a form which contains at least about 98 wt. % of the crystalline form. In an alternate embodiment, the invention is directed to suvorexant dodecyl sulfate isolated in a form which contains at least about 99 wt. % of the crystalline form.

In an alternate embodiment, the invention is directed to a pharmaceutical composition that comprises suvorexant dodecyl sulfate. In an alternate embodiment, the invention is directed to a pharmaceutical composition that comprises suvorexant dodecyl sulfate in a form which is at least about 40 wt. % of the crystalline form. In an alternate embodiment, the invention is directed to a pharmaceutical composition that comprises suvorexant dodecyl sulfate in a form which is at least about 50 wt. % of the crystalline form. In an alternate embodiment, the invention is directed to a pharmaceutical composition that comprises suvorexant dodecyl sulfate in a form which is at least about 60 wt. % of the crystalline form. In an alternate embodiment, the invention is directed to a pharmaceutical composition that comprises suvorexant dodecyl sulfate in a form which is at least about 70 wt. % of the crystalline form. In an alternate embodiment, the invention is directed to a pharmaceutical composition that comprises suvorexant dodecyl sulfate in a form which is at least about 80 wt. % of the crystalline form. In an alternate embodiment, the invention is directed to a pharmaceutical composition that comprises suvorexant dodecyl sulfate in a form which is at least about 90 wt. % of the crystalline form. In an alternate embodiment, the invention is directed to a pharmaceutical composition that comprises suvorexant dodecyl sulfate in a form which is at least about 95 wt. % of the crystalline form. In an alternate embodiment, the invention is directed to a pharmaceutical composition that comprises suvorexant dodecyl sulfate in a form which is at least about 98 wt. % of the crystalline form. In an alternate embodiment, the invention is directed to a pharmaceutical composition that comprises suvorexant dodecyl sulfate in a form which is at least about 99 wt. % of the crystalline form.

Suvorexant is disclosed as having activity in antagonizing the human orexin-1 (OX1) receptor with a Ki of 0.55 nM and in antagonizing the human orexin-2 (OX2) receptor with a Ki of 0.35 nM. The pKa of the free base of suvorexant did not appear to be amenable to salt formation, but surprisingly in accordance with the invention, salts were formed and provide unique and unexpected properties.

Pharmaceutically acceptable salts of suvorexant may have benefits relative to other morphological forms of suvorexant such as greater solubility and/or a faster dissolution rate than crystalline forms of the compound, which may improve bioavailability of the compound, may facilitate a faster onset of therapeutic action, may reduce variability of therapeutic response among subjects, and may reduce any food effect. The pharmaceutically acceptable salts of suvorexant exhibit comparable or improved in vivo bioavailability compared with formulations of other forms of suvorexant. The compound suvorexant is absorbed more rapidly after oral administration of these formulations. The AUC of the drug and the maximal concentration of the drug in the blood or serum are increased when a pharmaceutically acceptable salt of suvorexant is administered to a patient.

Pharmaceutically acceptable salts of suvorexant may be synthesized using a crystallization process that is more efficient and results in improved particle size and morphology control relative to other forms of suvorexant. Pharmaceutically acceptable salts of suvorexant may have better crystallinity, better filtration properties and gives better purity rejection than other forms of suvorexant. Pharmaceutically acceptable salts of suvorexant may have better processability for preparing formulations than other forms of suvorexant. Employing a pharmaceutically acceptable salt of suvorexant allows the use of conventional processing methods and formulation strategies. This is significant in that crystalline API forms typically have a reduced physical stability risk compared to the high energy state amorphous solid dispersions. Ultimately, this may allow for less protective and potentially less expensive packaging configurations. A conventional formulation also allows for the use of standard, well-known processing trains (roller compaction, blending, and compression). These standard processing trains have been optimized to provide high yield, are easily scalable, and are abundant throughout the pharmaceutical manufacturing world. In addition, the manufacture of non-standard formulations of suvorexant free base requires higher energy inputs (extrusion) or the use of solvents (spray drying). Thus, there is the potential for an overall lower cost manufacturing train with a conventional formulation strategy which may translate into a lower cost of goods X-ray powder diffraction studies are widely used to characterize molecular structures, crystallinity, and polymorphism. The X-ray powder diffraction patterns were generated on a Philips Analytical X'Pert PRO X-ray Diffraction System with PW3040/60 console. A PW3373/00 ceramic Cu (copper) LEF X-ray tube K-Alpha radiation was used as the source. In addition to obtaining X-ray powder diffraction patterns, samples were further characterized by solid-state carbon-13 nuclear magnetic resonance (NMR) spectra. The solid-state carbon-13 NMR spectra were obtained on a Bruker DSX 400WB NMR system using a Bruker 4 mm H/X CPMAS probe. The spectra were collected utilizing proton/carbon-13 variable-amplitude cross-polarization (VACP) at 80 kHz with a proton 90-degree pulse of 100 kHz, and SPINAL64 decoupling at 100 kHz. A Lorentzian line broadening of 30 Hz was applied to the spectra before Fourier Transformation. Chemical shifts are reported on the TMS scale using the carbonyl carbon of glycine (176.70 ppm.) as a secondary reference. Additional experimental parameters used for data acquisition were a pulse delay of 5 s, and signal averaging for 10240 scans. The magic-angle spinning (MAS) rate was set to 13 kHz and the sample temperature was set to 270 K. DSC data were acquired using TA Instruments DSC 2910 or equivalent instrumentation. A sample with a weight between 2 and 6 mg was weighed into a pan and the pan was crimped. This pan was placed in the sample position in the calorimeter cell. An empty pan was placed in the reference position. The calorimeter cell was closed and a flow of nitrogen is passed through the cell. The heating program was set to heat the sample at a heating rate of 10° C./min to a temperature of approximately 200° C. When the run was completed, the data were analyzed using the DSC analysis program in the system software. The observed endotherms were integrated between baseline temperature points that are above and below the temperature range over which the endotherm is observed. The data reported are the onset temperature, peak temperature and enthalpy. Raman spectroscopy is widely used to determine the composition and morphological character of samples of interest. FT-Raman (Fourier transform Raman) spectra were collected over the range of 50-4000 cm-1 with a Bruker IFS 66v/S system coupled with the FRA106/S Raman attachment. The signal was averaged for 5-10 minutes at a resolution of 4 cm-1 and a laser power of 300-500 mW. The samples were presented to the laser using a spinning stage which that was rotated during the measurement to provide a large sampling volume. The data observed may vary depending on the particular instrumentation, observation parameters and conditions of the sample employed.

Figure 1:
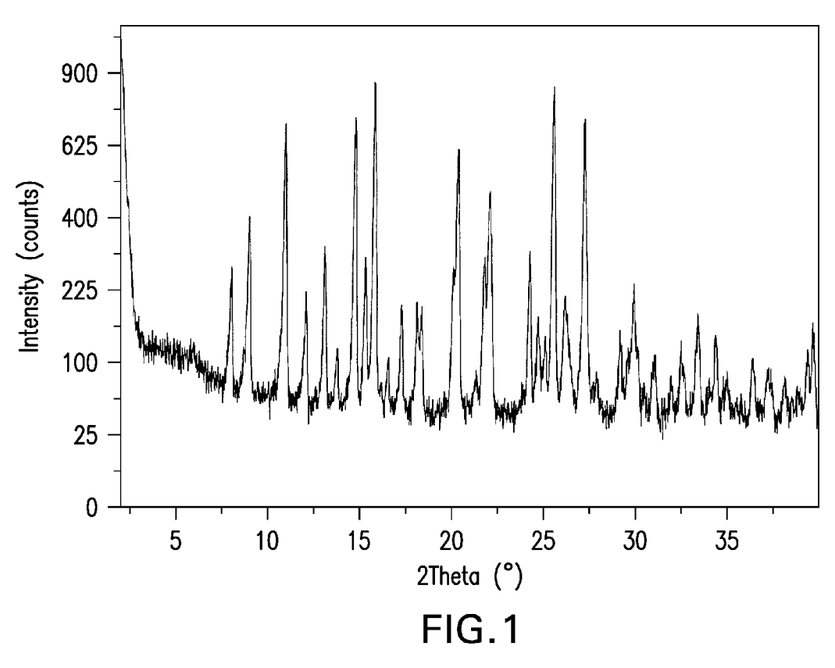
FIG. 1 shows an X-ray diffraction pattern of crystalline suvorexant hydrochloride.

FIG. 1 shows an X-ray powder diffraction pattern of crystalline suvorexant hydrochloride. Crystalline suvorexant hydrochloride exhibited characteristic diffraction peaks corresponding to d-spacings of 3.3, 3.5 and 42.5 angstroms. Crystalline suvorexant hydrochloride was further characterized by the d-spacings of 4.4, 5.6 and 6.0 angstroms. Crystalline suvorexant hydrochloride was even further characterized by the d-spacings of 4.0, 5.8 and 8.0 angstroms.

Characteristic Peak Position and d-Spacing for FIG. 1:

| Position [°2Th.] | Height [cts] | FWHM [°2Th.] | d-spacing [Å] | Relative Intensity [%] |
|---|---|---|---|---|
| 2.076 | 700.05 | 0.2007 | 42.55683 | 92.96 |
| 8.0661 | 119.86 | 0.0836 | 10.96148 | 15.92 |
| 9.0607 | 195 | 0.0669 | 9.76027 | 25.89 |
| 11.0103 | 374.2 | 0.1004 | 8.03604 | 49.69 |
| 12.0975 | 79.89 | 0.1338 | 7.31618 | 10.61 |
| 13.1161 | 159.62 | 0.0836 | 6.75017 | 21.2 |
| 13.7204 | 60.36 | 0.1338 | 6.4542 | 8.02 |
| 14.7527 | 670.4 | 0.1338 | 6.00482 | 89.02 |
| 15.3066 | 213.93 | 0.1004 | 5.78876 | 28.41 |
| 15.8286 | 495.49 | 0.1673 | 5.59901 | 65.8 |
| 16.5454 | 49.77 | 0.1338 | 5.35801 | 6.61 |
| 17.2921 | 125.62 | 0.1338 | 5.12829 | 16.68 |
| 18.1035 | 95.65 | 0.1673 | 4.90023 | 12.7 |
| 18.3665 | 93 | 0.1338 | 4.83066 | 12.35 |
| 20.0607 | 182.8 | 0.1338 | 4.42635 | 24.28 |
| 20.3886 | 399.37 | 0.1673 | 4.35589 | 53.03 |
| 22.048 | 327.51 | 0.1338 | 4.03167 | 43.49 |
| 24.2635 | 155.56 | 0.1673 | 3.66832 | 20.66 |
| 24.7243 | 102.31 | 0.1338 | 3.601 | 13.59 |
| 25.5821 | 753.05 | 0.184 | 3.48215 | 100 |
| 26.1202 | 149.6 | 0.1673 | 3.41164 | 19.87 |
| 27.2265 | 681.58 | 0.1506 | 3.27547 | 90.51 |
| 29.2057 | 61.4 | 0.2342 | 3.05785 | 8.15 |
| 29.889 | 111.91 | 0.2007 | 2.98948 | 14.86 |
| 30.9865 | 68.96 | 0.2342 | 2.88605 | 9.16 |
| 32.5078 | 43.68 | 0.2676 | 2.75439 | 5.8 |
| 33.3312 | 87.07 | 0.2342 | 2.6882 | 11.56 |
| 34.3689 | 81.38 | 0.1338 | 2.60938 | 10.81 |
| 36.4115 | 47.23 | 0.1338 | 2.46755 | 6.27 |
| 37.2355 | 34.23 | 0.2676 | 2.41482 | 4.55 |
| 38.1313 | 37.14 | 0.1338 | 2.36012 | 4.93 |
| 39.6314 | 72.11 | 0.1338 | 2.27418 | 9.58 |

Figure 2:
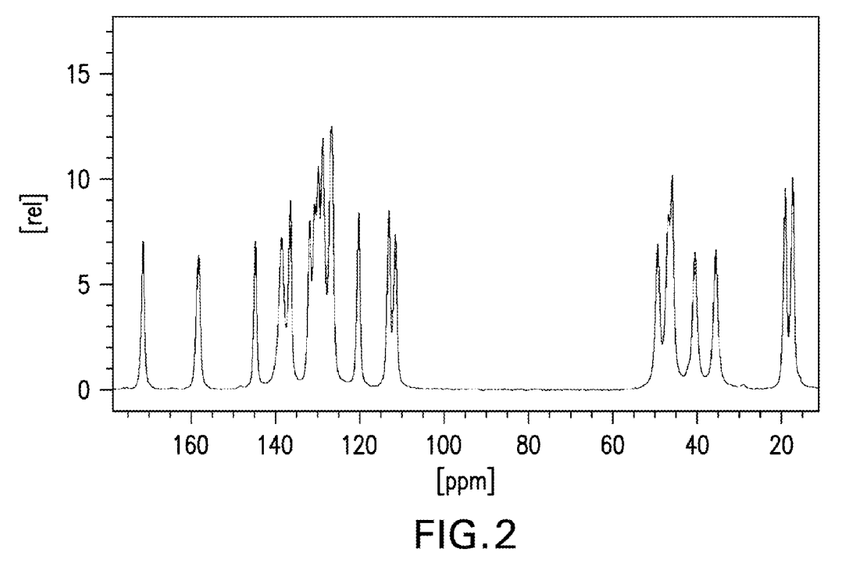
FIG. 2 shows a carbon-13 cross-polarization magic-angle spinning (CPMAS) nuclear magnetic resonance (NMR) spectrum of suvorexant hydrochloride.

FIG. 2 shows a carbon-13 cross-polarization magic-angle spinning (CPMAS) nuclear magnetic resonance (NMR) spectrum of crystalline suvorexant hydrochloride. Crystalline suvorexant hydrochloride was characterized by carbon-13 cross-polarization magic-angle spinning (CPMAS) nuclear magnetic resonance (NMR) peaks corresponding to 126.9, 128.9 and 130.0 p.p.m. Crystalline suvorexant hydrochloride was further characterized by peaks corresponding to 45.9, 17.4 and 19.1 p.p.m. Crystalline suvorexant hydrochloride was even further characterized by peaks corresponding to 136.7, 130.8 and 113.1 p.p.m.

Characteristic Carbon-13 Cross-Polarization Magic-Angle Spinning Nuclear Magnetic Resonance Peaks for FIG. 2:

| Peak | [ppm] |
|---|---|
| 1 | 171.3 |
| 2 | 158.2 |
| 3 | 144.8 |
| 4 | 138.7 |
| 5 | 136.7 |
| 6 | 132.0 |
| 7 | 130.8 |
| 8 | 130.0 |
| 9 | 128.9 |
| 10 | 126.9 |
| 11 | 120.3 |
| 12 | 113.1 |
| 13 | 111.6 |
| 14 | 49.3 |
| 15 | 46.8 |
| 16 | 45.9 |
| 17 | 40.5 |
| 18 | 35.6 |
| 19 | 19.1 |
| 20 | 17.4 |

Figure 3:
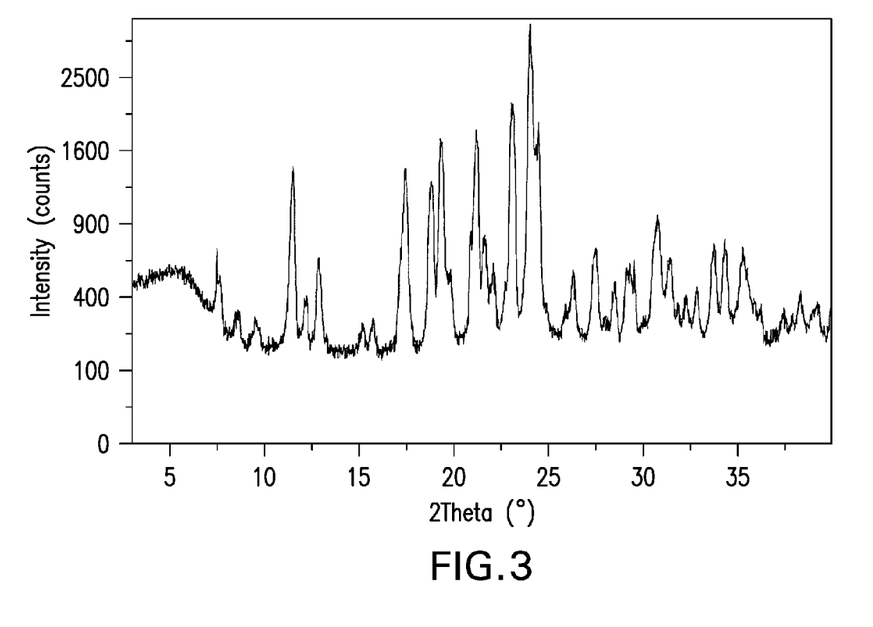
FIG. 3 shows an X-ray powder diffraction pattern of crystalline suvorexant hydrochloride methanol solvate.

FIG. 3 shows an X-ray powder diffraction pattern of crystalline suvorexant hydrochloride methanol solvate. Crystalline suvorexant hydrochloride methanol solvate exhibited characteristic diffraction peaks corresponding to d-spacings of 3.6, 3.7 and 3.9 angstroms. Crystalline suvorexant hydrochloride methanol solvate was further characterized by the d-spacings of 4.2, 4.6 and 7.7 angstroms.

Crystalline suvorexant hydrochloride methanol solvate was further characterized by DSC themal analysis that showed two melting point endotherms at 121 and 152° C., respectively with corresponding weight losses by TGA.

Characteristic Peak Position and d-Spacing for FIG. 3:

| Position [°2Th.] | d-spacing [Å] | Relative Intensity [%] |
|---|---|---|
| 7.5292 | 11.74189 | 15.85 |
| 7.7343 | 11.43091 | 9.95 |
| 8.6913 | 10.17431 | 4.85 |
| 9.6047 | 9.20868 | 3.98 |
| 11.5188 | 7.68241 | 42.12 |
| 12.2182 | 7.24414 | 7.5 |
| 12.8763 | 6.87535 | 15.49 |
| 15.2336 | 5.81632 | 3.19 |
| 15.76 | 5.62323 | 3.98 |
| 17.4494 | 5.08243 | 39.57 |
| 18.7128 | 4.74203 | 29.19 |
| 18.9007 | 4.6953 | 34.65 |
| 19.2762 | 4.6047 | 45.83 |
| 19.8299 | 4.47734 | 11.95 |
| 21.3127 | 4.16908 | 41.7 |
| 21.6298 | 4.10866 | 19.59 |
| 22.1253 | 4.01776 | 14.48 |
| 22.9908 | 3.86843 | 56.53 |
| 23.2235 | 3.83019 | 50.63 |
| 24.0414 | 3.70171 | 100 |
| 24.4904 | 3.63485 | 55.36 |
| 26.3397 | 3.38371 | 12.73 |
| 27.522 | 3.24097 | 17.58 |
| 28.5348 | 3.1282 | 10.36 |
| 29.1335 | 3.06526 | 12.95 |
| 29.5544 | 3.02256 | 13.78 |
| 30.782 | 2.90476 | 26.19 |
| 31.431 | 2.84625 | 15.41 |
| 32.2545 | 2.77543 | 7.32 |
| 32.8193 | 2.72895 | 9.3 |
| 33.725 | 2.65771 | 18.42 |
| 34.3201 | 2.61297 | 19.1 |
| 35.278 | 2.54419 | 18.05 |
| 36.1708 | 2.48342 | 5.71 |
| 37.42 | 2.40333 | 4.79 |
| 38.3188 | 2.349 | 8.36 |
| 39.21 | 2.29764 | 6.37 |

Figure 4:
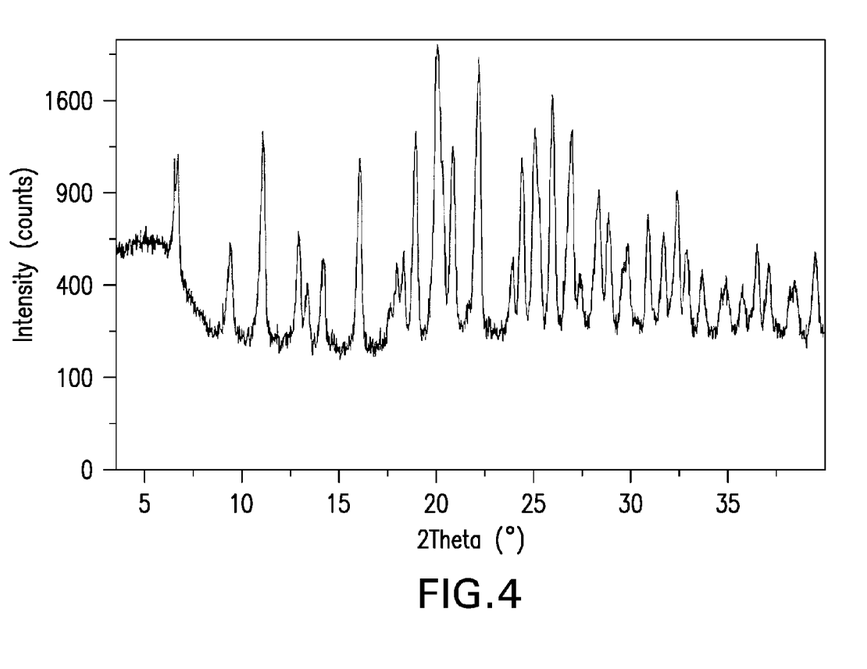
FIG. 4 shows an X-ray powder diffraction pattern of crystalline suvorexant hydrochloride ethanol solvate.

FIG. 4 shows an X-ray powder diffraction pattern of crystalline suvorexant hydrochloride ethanol solvate. Crystalline suvorexant hydrochloride ethanol solvate exhibited characteristic diffraction peaks corresponding to d-spacings of 3.4, 4.0 and 4.7 angstroms. Crystalline suvorexant hydrochloride ethanol solvate was further characterized by the d-spacings of 3.6, 4.2 and 8.0 angstroms.

Characteristic Peak Position and d-Spacing for FIG. 4:

| Position [°2Th.] | d-spacing [Å] | Relative Intensity [%] |
|---|---|---|
| 6.5208 | 13.55519 | 43.82 |
| 6.6855 | 13.22154 | 51.77 |
| 9.3897 | 9.41898 | 21.14 |
| 11.0521 | 8.0057 | 60.52 |
| 12.889 | 6.8686 | 23.63 |
| 13.3475 | 6.63369 | 10.22 |
| 14.1414 | 6.26302 | 16.83 |
| 16.0186 | 5.53301 | 50.92 |
| 17.9591 | 4.9393 | 15.35 |
| 18.3008 | 4.84786 | 18.88 |
| 18.9197 | 4.69065 | 62.05 |
| 20.1102 | 4.41557 | 100 |
| 20.3614 | 4.36165 | 41.59 |
| 20.8502 | 4.2605 | 55.77 |
| 22.1634 | 4.01094 | 97.64 |
| 23.9103 | 3.72171 | 16.3 |
| 24.3816 | 3.65082 | 50.71 |
| 25.0408 | 3.5562 | 64.59 |
| 25.2916 | 3.52149 | 33.72 |
| 25.9418 | 3.43468 | 77.96 |
| 26.9256 | 3.31138 | 63.12 |
| 27.3719 | 3.2584 | 11.94 |
| 28.2964 | 3.15401 | 38.77 |
| 28.8134 | 3.09858 | 31.28 |
| 29.8056 | 2.99765 | 21.56 |
| 30.8497 | 2.89854 | 29.93 |
| 31.6411 | 2.82782 | 24.21 |
| 32.3481 | 2.76762 | 37.26 |
| 32.8226 | 2.72868 | 18.88 |
| 33.6372 | 2.66444 | 13.52 |
| 34.8536 | 2.57419 | 11.2 |
| 35.7043 | 2.51479 | 9.53 |
| 36.4792 | 2.46312 | 20.92 |
| 37.0776 | 2.42473 | 15.37 |
| 38.3843 | 2.34515 | 10.48 |
| 39.4646 | 2.2834 | 19.23 |

Figure 5:
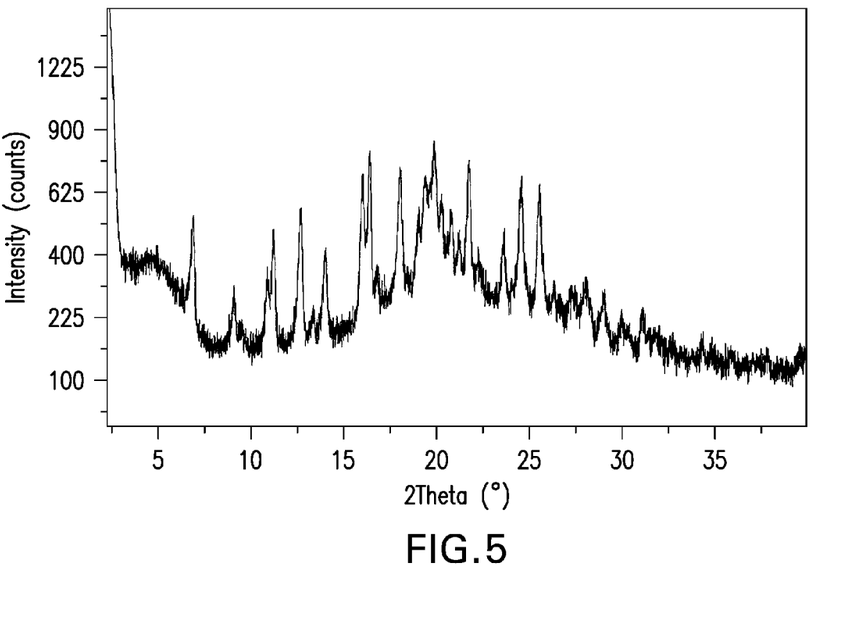
FIG. 5 shows an X-ray powder diffraction pattern of crystalline suvorexant methanesulfonate.

FIG. 5 shows an X-ray powder diffraction pattern of crystalline suvorexant methanesulfonate. Crystalline suvorexant methanesulfonate exhibited characteristic diffraction peaks corresponding to d-spacings of 4.1, 4.5 and 5.4 angstroms. Crystalline suvorexant methanesulfonate was further characterized by the d-spacings of 4.6, 4.9 and 5.5 angstroms.

Characteristic Peak Position and d-Spacing for FIG. 5:

| Position [°2Th.] | d-spacing [Å] | Relative Intensity [%] |
|---|---|---|
| 6.8308 | 12.94075 | 57.31 |
| 9.0163 | 9.80827 | 18.56 |
| 10.8303 | 8.16918 | 26.3 |
| 11.1614 | 7.92759 | 46.96 |
| 12.645 | 7.00057 | 61.13 |
| 13.3 | 6.65726 | 11.88 |
| 14.0045 | 6.32393 | 39.97 |
| 15.9748 | 5.54808 | 82.14 |
| 16.3964 | 5.40636 | 95.74 |
| 18.0334 | 4.91912 | 85.87 |
| 19.0064 | 4.66943 | 55.97 |
| 19.3479 | 4.58777 | 81.45 |
| 19.8572 | 4.47126 | 100 |
| 20.2505 | 4.38529 | 67.04 |
| 20.7958 | 4.27152 | 58.33 |
| 21.2038 | 4.19025 | 46.55 |
| 21.6884 | 4.0977 | 90.01 |
| 22.2432 | 3.99674 | 35.25 |
| 23.5777 | 3.77345 | 42.31 |
| 24.5479 | 3.62647 | 76.54 |
| 25.545 | 3.48714 | 74.83 |
| 26.3027 | 3.38837 | 21.81 |
| 27.2316 | 3.27486 | 20.52 |
| 28.0363 | 3.18267 | 24.76 |
| 28.9653 | 3.08268 | 18.59 |
| 29.9659 | 2.98198 | 10.2 |
| 31.115 | 2.87443 | 13.39 |
| 34.2823 | 2.61577 | 4.99 |
| 35.8796 | 2.5029 | 2.67 |
| 37.8508 | 2.37696 | 3.13 |

Figure 6:
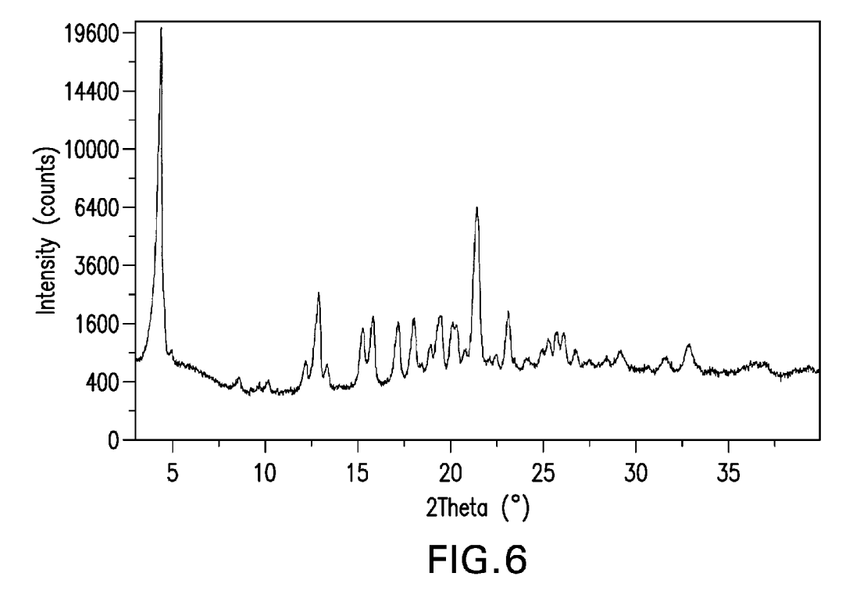
FIG. 6 shows an X-ray powder diffraction pattern of crystalline suvorexant dodecyl sulfate.

FIG. 6 shows an X-ray powder diffraction pattern of crystalline suvorexant dodecyl sulfate. Crystalline suvorexant dodecyl sulfate exhibited characteristic diffraction peaks corresponding to d-spacings of 4.1, 4.2 and 20.3 angstroms. Crystalline suvorexant dodecyl sulfate was further characterized by the d-spacings of 3.8, 5.6 and 6.9 angstroms.

Characteristic Peak Position and d-Spacing for FIG. 6:

| Position [°2Th.] | d-spacing [Å] | Relative Intensity [%] |
|---|---|---|
| 4.3433 | 20.3448 | 100 |
| 4.9277 | 17.9332 | 3.27 |
| 8.5951 | 10.28789 | 0.83 |
| 10.1499 | 8.71521 | 0.57 |
| 12.1914 | 7.26001 | 2 |
| 12.8805 | 6.87313 | 11.45 |
| 13.3176 | 6.64852 | 1.76 |
| 15.2835 | 5.79745 | 5.66 |
| 15.8353 | 5.59666 | 6.89 |
| 17.1748 | 5.16307 | 6.48 |
| 18.0472 | 4.91538 | 6.75 |
| 18.9493 | 4.68338 | 3.44 |
| 19.5248 | 4.54661 | 6.79 |
| 20.1282 | 4.41165 | 6.05 |
| 20.3442 | 4.3653 | 5.96 |
| 20.8283 | 4.26492 | 2.8 |
| 21.3545 | 4.15757 | 24.92 |
| 21.4545 | 4.14183 | 30.57 |
| 22.5106 | 3.94986 | 2.3 |
| 23.178 | 3.83762 | 7.77 |
| 24.1755 | 3.68148 | 1.83 |
| 24.97 | 3.56611 | 2.68 |
| 25.3223 | 3.5173 | 3.86 |
| 25.757 | 3.45891 | 4.72 |
| 26.139 | 3.40923 | 4.67 |
| 26.7854 | 3.3284 | 2.61 |
| 28.4255 | 3.13998 | 1.7 |
| 29.1574 | 3.06281 | 2.37 |
| 31.5903 | 2.83225 | 1.61 |
| 32.8524 | 2.72628 | 2.93 |
| 36.453 | 2.46484 | 0.92 |
| 37.0372 | 2.42729 | 0.91 |

Crystalline suvorexant p-toluenesulfonate exhibited characteristic diffraction peaks corresponding to d-spacings of 6.4, 8.0 and 16.2 angstroms. Crystalline suvorexant p-toluenesulfonate was further characterized by the d-spacings of 4.5, 5.5 and 10.7 angstroms.

Crystalline suvorexant p-toluenesulfonate was further characterized by DSC themal analysis that showed a melting point endotherm at 157.9° C., with corresponding weight losses by TGA.

Characteristic Peak Position and d-Spacing for Crystalline Suvorexant p-Toluenesulfonate:

| Position [°2Th.] | d-spacing [Å] | Relative Intensity [%] |
|---|---|---|
| 5.4688 | 16.16021 | 100.00 |
| 8.2724 | 10.68856 | 14.01 |
| 11.0823 | 7.98396 | 35.03 |
| 12.9005 | 6.86249 | 2.32 |
| 13.3361 | 6.63933 | 1.40 |
| 13.9035 | 6.36963 | 21.25 |
| 16.0359 | 5.52708 | 10.50 |
| 16.7250 | 5.30089 | 8.78 |
| 17.8231 | 4.97668 | 5.19 |
| 18.5005 | 4.79598 | 2.36 |
| 19.3056 | 4.59775 | 4.00 |
| 19.5664 | 4.53704 | 9.57 |
| 20.5046 | 4.33152 | 5.39 |
| 21.0276 | 4.22496 | 5.95 |
| 21.6307 | 4.10850 | 2.25 |
| 22.4247 | 3.96480 | 4.61 |
| 22.7509 | 3.90868 | 3.64 |
| 22.9950 | 3.86774 | 5.80 |
| 23.3384 | 3.81160 | 2.97 |
| 24.0993 | 3.69295 | 3.01 |
| 25.1463 | 3.54151 | 6.08 |
| 26.0819 | 3.41656 | 6.44 |
| 27.0332 | 3.29845 | 2.33 |
| 27.8145 | 3.20755 | 3.02 |
| 29.8324 | 2.99502 | 2.08 |
| 30.4789 | 2.93295 | 1.08 |
| 31.0561 | 2.87974 | 1.14 |
| 31.8912 | 2.80622 | 0.66 |
| 33.9752 | 2.63871 | 1.81 |
| 35.3245 | 2.54095 | 0.58 |
| 37.7484 | 2.38318 | 0.19 |

Oral administration of a pharmaceutically acceptable salt of suvorexant may surprisingly reduce the food effect, that is, oral administration of a formulation comprising a pharmaceutically acceptable salt of suvorexant may provide substantially the same suvorexant exposure and less variability in bioavailability across a patient population regardless of whether the formulation is administered under Fed Conditions or Fasted Conditions. Moreover, when the results of oral administration of a formulation comprising a pharmaceutically acceptable salt of suvorexant are compared to those obtained after administration of an equivalent amount of suvorexant in the form of a conventional formulation, under either fed conditions or fasted conditions, the pharmaceutically acceptable salts of suvorexant may provide increased bioavailability, with lower variability in bioavailability across a population of subjects, and higher exposure levels (AUC) in healthy volunteers to whom it is administered. Moreover, it is believed that similar results are achieved in patients to whom formulation comprising a pharmaceutically acceptable salt of suvorexant is administered.

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particular embodiments include the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. When the compound employed in the invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particular embodiments include the citric, hydrobromic, hydrochloric, maleic, phosphoric, sulfuric, fumaric, and tartaric acids. It will be understood that, as used herein, references to suvorexant are meant to also include the pharmaceutically acceptable salts.

Exemplifying the invention is the use of the compounds disclosed in the Examples and herein. A pharmaceutically acceptable salt of suvorexant is useful in a method of antagonizing orexin receptor activity in a patient such as a mammal in need of such inhibition comprising the administration of an effective amount of the compound. The invention is directed to the use of a pharmaceutically acceptable salt of suvorexant or a pharmaceutically acceptable salt thereof as antagonists of orexin receptor activity. In addition to primates, especially humans, it is possible that a variety of other mammals may be treated according to the method of the invention.

The subject treated in the methods of the invention is generally a mammal, such as a human being, male or female. The term "therapeutically effective amount" means the amount of the subject compound that will elicit the biological or medical response of a tissue, system, animal or human that is being sought by the researcher, veterinarian, medical doctor or other clinician. It is recognized that one skilled in the art may affect the neurological and psychiatric disorders by treating a patient presently afflicted with the disorders or by prophylactically treating a patient afflicted with the disorders with an effective amount of the compound of the invention. As used herein, the terms "treatment" and "treating" refer to all processes wherein there may be a slowing, interrupting, arresting, controlling, or stopping of the progression of the neurological and psychiatric disorders described herein, but does not necessarily indicate a total elimination of all disorder symptoms, as well as the prophylactic therapy of the mentioned conditions, particularly in a patient who is predisposed to such disease or disorder. The terms "administration of" and or "administering a" compound should be understood to mean providing a compound of the invention or a prodrug of a compound of the invention to the individual in need thereof.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the invention encompass any composition made by admixing a pharmaceutically acceptable of suvorexant and a pharmaceutically acceptable carrier. By "pharmaceutically acceptable" it is meant the carrier, diluent or excipient must be compatible with the other ingredients of the formulation and not deleterious to the recipient thereof.

The scientific literature has implicated the orexin receptors in a wide range of biological functions. This has suggested a potential role for these receptors in a variety of disease processes in humans or other species. In accordance with the invention, a pharmaceutically acceptable salt of suvorexant may have utility in treating, preventing, ameliorating, controlling or reducing the risk of neurological and psychiatric disorders associated with orexin receptors. In accordance with the invention, a pharmaceutically acceptable salt of suvorexant may provide methods for: preventing and treating sleep disorders and sleep disturbances; treating insomnia; enhancing the quality of sleep; augmenting sleep maintenance; increasing REM sleep; increasing stage 2 sleep; decreasing fragmentation of sleep patterns; treating insomnia; enhancing cognition; increasing memory retention; treating or controlling obesity; treating or controlling depression; in a mammalian patient in need thereof which comprises administering to the patient a therapeutically effective amount of a pharmaceutically acceptable salt of suvorexant of the invention.

In accordance with the invention, a pharmaceutically acceptable salt of suvorexant may also be useful in a method for the prevention, treatment, control, amelioration, or reduction of risk of the diseases, disorders and conditions noted herein. The dosage of active ingredient in the compositions of this invention may be varied, however, it is necessary that the amount of the active ingredient be such that a suitable dosage form is obtained. The active ingredient may be administered to patients (animals and human) in need of such treatment in dosages that will provide optimal pharmaceutical efficacy. The selected dosage depends upon the desired therapeutic effect, on the route of administration, and on the duration of the treatment. The dose will vary from patient to patient depending upon the nature and severity of disease, the patient's weight, special diets then being followed by a patient, concurrent medication, and other factors which those skilled in the art will recognize. Generally, dosage levels of between 0.0001 to 10 mg/kg. of body weight daily are administered to the patient, e.g., humans and elderly humans, to obtain effective antagonism of orexin receptors. The dosage range will generally be about 0.5 mg to 1.0 g. per patient per day which may be administered in single or multiple doses. In one embodiment, the dosage range will be about 0.5 mg to 500 mg per patient per day; in another embodiment about 0.5 mg to 200 mg per patient per day; and in yet another embodiment about 5 mg to 50 mg per patient per day. Pharmaceutical compositions of the invention may be provided in a solid dosage formulation such as comprising about 0.5 mg to 500 mg active ingredient, or comprising about 1 mg to 250 mg active ingredient. The pharmaceutical composition may be provided in a solid dosage formulation comprising about 1 mg, 5 mg, 10 mg, 15 mg, 20 mg, 25 mg, 30 mg, 40 mg, 50 mg, or 100 mg active ingredient. In specific embodiments, the pharmaceutical composition may be provided in a solid dosage formulation comprising about 10 mg, 15 mg, 20 mg, 30 mg, or 40 mg active ingredient. For oral administration, the compositions may be provided in the form of tablets containing 1.0 to 1000 milligrams of the active ingredient, such as 1, 5, 10, 15, 20, 25, 50, 75, 100, 150, 200, 250, 300, 400, 500, 600, 750, 800, 900, and 1000 milligrams of the active ingredient for the symptomatic adjustment of the dosage to the patient to be treated. The compound may be administered on a regimen of 1 to 4 times per day, such as once or twice per day. In an embodiment of the invention, the compound may be administered in a regimen of once per day in the evening, such as prior to initiating sleep.

A pharmaceutically acceptable salt of suvorexant that is employed in the invention may be used in combination with one or more other drugs in the treatment, prevention, control, amelioration, or reduction of risk of diseases or conditions for which compounds of the invention or the other drugs may have utility, where the combination of the drugs together are safer or more effective than either drug alone. Such other drug(s) may be administered, by a route and in an amount commonly used therefor, contemporaneously or sequentially with a compound of the invention. When a compound of the invention is used contemporaneously with one or more other drugs, a pharmaceutical composition in unit dosage form containing such other drugs and the compound of the invention is contemplated. However, the combination therapy may also include therapies in which the compound of the invention and one or more other drugs are administered on different overlapping schedules. It is also contemplated that when used in combination with one or more other active ingredients, the compounds of the invention and the other active ingredients may be used in lower doses than when each is used singly. Accordingly, the pharmaceutical compositions of the invention include those that contain one or more other active ingredients, in addition to a compound of the invention. The above combinations include combinations of a compound of the invention not only with one other active compound, but also with two or more other active compounds.

Likewise, the pharmaceutically acceptable salt of suvorexant thereof that is employed in the invention may be used in combination with other drugs that are used in the prevention, treatment, control, amelioration, or reduction of risk of the diseases or conditions for which compounds of the invention are useful. Such other drugs may be administered, by a route and in an amount commonly used therefor, contemporaneously or sequentially with a compound of the invention. When a pharmaceutically acceptable salt of suvorexant is used contemporaneously with one or more other drugs, a pharmaceutical composition containing such other drugs in addition to the compound of the invention is contemplated. Such pharmaceutical compositions are prepared without undue experimentation in accordance with the methods described herein and known in the art. Accordingly, the pharmaceutical compositions include those that also contain one or more other active ingredients, in addition to a compound of the invention.

The weight ratio of a pharmaceutically acceptable salt of suvorexant to the second active ingredient may be varied and will depend upon the effective dose of each ingredient. Generally, an effective dose of each will be used. Thus, for example, when a pharmaceutically acceptable salt of suvorexant is combined with another agent, the weight ratio of the compound of the pharmaceutically acceptable salt of suvorexant to the other agent will generally range from about 1000:1 to about 1:1000, such as about 200:1 to about 1:200. Combinations of a pharmaceutically acceptable salt of suvorexant and other active ingredients will generally also be within the aforementioned range, but in each case, an effective dose of each active ingredient should be used. In such combinations the pharmaceutically acceptable salt of suvorexant and other active agents may be administered separately or in conjunction. In addition, the administration of one element may be prior to, concurrent to, or subsequent to the administration of other agent(s).

A pharmaceutical salt of suvorexant may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

Pharmaceutical compositions intended for oral use may be prepared in accordance with the methods described herein and other method known to the art for the manufacture of pharmaceutical compositions. Such compositions may further contain one or more agents selected from the group consisting of sweetening agents, flavoring agents, coloring agents and preserving agents in order to provide pharmaceutically elegant and palatable preparations. Tablets may contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastro-intestinal tract and thereby provide a sustained action over a longer period. Compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Aqueous suspensions contain the active materials in admixture with excipients suitable for the manufacture of aqueous suspensions. Dispersible powders and granules suitable for preparation of an aqueous suspension by the addition of water provide the active ingredient in admixture with a dispersing or wetting agent, suspending agent and one or more preservatives.

Methods for preparing the compounds of this invention are illustrated herein. Starting materials are made according to procedures known in the art or as illustrated herein. The following abbreviations may be used herein: 2-MeTHF: 2-methyltetrahydrofuran; Ac: acetyl; Ar: aryl; AY: assay yield; Bn: benzyl; Boc: tert-butyloxy carbonyl; Boc$_2$O: di-tert-butyldicarbonate; BSA: bovine serum albumin; Cbz: carbobenzyloxy; CDI: carbonyl diimidazole; CSA: camphor sulfonic acid; DEAD: diethylazodicarboxylate; DCE: dichloroethane; DCM: dichloromethane; DIPEA: N,N-di-isopropylethylamine; DMF: N,N-dimethylformamide; DMSO: dimethylsulfoxide; EDC: N-(3-dimethylaminopropyl)-N'-ethylcarbodiimide; Et: ethyl; EtOH: ethanol; Et$_3$N: triethylamine; GC-FID: gas chromatography-flame ionization detector; HOBT: hydroxybenzotriazole hydrate; HPLC: high performance liquid chromatography; LC-MS: liquid chromatography-mass spectrometry; LRMS: low resolution mass spectrometry; Me: methyl; MTBE: methyl tert-butyl ether; Ph: phenyl; PhMe: toluene; rt: room temperature; SOCl$_2$: thionyl chloride; T$_3$P: 1-propylphosphonic anhydride; t-Bu: tert-butyl; TsCl: tosyl chloride; TFA: trifluoroacetic acid; THF: tetrahydrofuran. Pharmaceutically acceptable salts of suvorexant of the invention can be prepared in a variety of fashions. In some cases the final product may be further modified, for example, by drying, hydration or solvation. In some cases the order of carrying out the procedures may be varied. The following examples are provided so that the invention might be more fully understood. These examples are illustrative only and should not be construed as limiting the invention in any way.

Example 1

Preparation of Suvorexant Hydrochloride Methanol Solvate

Suvorexant (49.78 mg) was added to a 4 mL vial followed by 0.5 ml of methanol. To the vial was added 1 eq. of HCl as a 0.1 M solution in diethyl ether and the vial was heated to 50° C. for 1 hour. The volatile solvents removed by evaporation overnight. To the vial was added 0.5 mL methyl tert-butyl ether and the vial was heated to 65° C. for 1 hour. Alternately, isopropyl acetate was used instead of methyl tert-butyl ether. The mixture was stirred as a slurry and slowly cooled over 4 hours with seeding with suvorexant hydrochloride. The solution was vacuum frit filtered to give suvorexant hydrochloride methanol solvate.

Example 2

Preparation of Suvorexant Methanesulfonate

Suvorexant sulfate (48.44 mg) was added to a 4 mL vial followed by 0.5 mL of 1:3 ethanol/isopropyl acetate. The vial was heated to 65° C. for 1 hour while stirring. Seeded with suvorexant meslyate and allowed to cool to room temperature for 12 hours. The solution was vacuum frit filtered to give suvorexant methanesulfonate, which was dried in a 40° C. vacuum oven for 30 minutes.

Example 3

Preparation of Suvorexant p-Tolunesulfonate

Suvorexant (49.06 mg) was added to a 4 mL vial followed by 1 equivalent p-toluene sulfonic acid as a 0.1 M solution in tetrahydrofuran. The vial was heated to 65° C. for 1 hour with stirring. The volatile solvents removed by Genevac at 40° C. To the vial was added 0.5 mL ethyl acetate and the vial was heated to 65° C. for 1 hour. The mixture was stirred as a slurry and allowed to cool to room temperature for 12 hours with seeding. The solution was vacuum frit filtered to give suvorexant p-toluenesulfonate, which was dried in a 40° C. vacuum oven for 30 minutes.

Example 4

Preparation of Suvorexant Dodecyl Sulfate

Suvorexant (250 mg) was dissolved in 5 ml acetonitrile by heating at 40° C. To the solution was added one mole equivalent of sodium dodecyl sulfate (solid), followed by 1 ml water to give a clear solution. A portion of this solution (0.25 ml) was acidified by adding 0.5 ml of aqueous 0.5 N HCl. The solution was allowed to cool to room temperature and then vacuum frit filtered to give suvorexant dodecyl sulfate.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention.

What is claimed is:

1. Crystalline suvorexant hydrochloride which is characterized by a solid-state carbon-13 cross-polarization magic-angle spinning nuclear magnetic resonance spectrum having peaks corresponding to 17.4, 19.1, 45.9, 126.9, 128.9 and 130.0 p.p.m.

2. The crystalline suvorexant hydrochloride of claim 1 which is further characterized by an x-ray powder diffraction pattern, collected using copper K-alpha radiation, exhibiting characteristic diffraction peaks corresponding to d-spacings of 3.3, 3.5, 4.4, 5.6, 6.0 and 42.5 angstroms.

3. Crystalline suvorexant methanesulfonate characterized by an x-ray powder diffraction pattern, collected using copper K-alpha radiation, having at least five characteristic peaks selected from the group consisting of 12.6, 16.0, 16.4, 18.0, 19.3, 19.8, 20.2, 21.7, 24.5 and 25.5° 2Theta.

4. The crystalline suvorexant methanesulfonate of claim 3 which is further characterized by an x-ray powder diffraction pattern exhibiting characteristic diffraction peaks corresponding to d-spacings of 4.1, 4.5, 4.6, 4.9, 5.4 and 5.5 angstroms.

5. Crystalline suvorexant dodecyl sulfate characterized by an x-ray powder diffraction pattern, collected using copper K-alpha radiation, having at least five characteristic peaks selected from the group consisting of 4.3, 12.9, 15.8, 18.0, 19.5, 21.4, 21.5 and 23.2° 2Theta.

6. The crystalline suvorexant dodecyl sulfate of claim 5 which is further characterized by an x-ray powder diffraction pattern having d-spacings of 3.8, 4.1, 4.2, 5.6, 6.9 and 20.3 angstroms.

7. Crystalline suvorexant p-toluenesulfonate characterized by an x-ray powder diffraction pattern, collected using copper K-alpha radiation, having at least five characteristic peaks selected from the group consisting of 5.5, 8.3, 11.1, 13.9, 16.0, 16.7, 19.6 and 26.1° 2Theta.

8. Crystalline suvorexant p-toluenesulfonate of claim 7 which is further characterized by an x-ray powder diffraction pattern exhibiting characteristic diffraction peaks corresponding to d-spacings of 4.5, 5.5, 6.4, 8.0, 10.7 and 16.2 angstroms.

9. Crystalline suvorexant p-toluenesulfonate of claim 7 which is further characterized by DSC themal analysis that shows a melting point endotherm at 157.9° C.

10. A pharmaceutical composition comprising suvorexant hydrochloride of claim 1 and a pharmaceutically acceptable carrier.

11. A pharmaceutical composition comprising suvorexant methanesulfonate of claim 3 and a pharmaceutically acceptable carrier.

12. A pharmaceutical composition comprising suvorexant dodecyl sulfate of claim 5 and a pharmaceutically acceptable carrier.

13. A pharmaceutical composition comprising suvorexant p-toluenesulfonate of claim 7 and a pharmaceutically acceptable carrier.

14. A method for treating insomnia in a human patient in need thereof which comprises administering to the patient a therapeutically effective amount of suvorexant hydrochloride of claim 1.

15. A method for treating insomnia in a human patient in need thereof which comprises administering to the patient a therapeutically effective amount of suvorexant methanesulfonate of claim 3.

16. A method for treating insomnia in a human patient in need thereof which comprises administering to the patient a therapeutically effective amount of suvorexant dodecyl sulfate of claim 5.

17. A method for treating insomnia in a human patient in need thereof which comprises administering to the patient a therapeutically effective amount of suvorexant p-toluenesulfonate of claim 7.

* * * * *